United States Patent [19]

Qi et al.

[11] Patent Number: 5,371,279
[45] Date of Patent: Dec. 6, 1994

[54] ACETIC ACID REMOVAL FROM LIQUID ETHER ACETATES

[75] Inventors: Jian S. Qi, Amherst; Garra C. Lester, Eden, both of N.Y.

[73] Assignee: Occidental Chemical Corporation, Niagara Falls, N.Y.

[21] Appl. No.: 210,853

[22] Filed: Mar. 21, 1994

[51] Int. Cl.$^5$ ............................................... C07C 67/02
[52] U.S. Cl. .................................... 560/263; 560/265
[58] Field of Search ................................ 560/263, 265

[56] References Cited

U.S. PATENT DOCUMENTS

| | | | |
|---|---|---|---|
| 4,004,069 | 1/1977 | Bernhardt et al. | 525/371 |
| 4,082,777 | 4/1978 | Fisher et al. | 549/525 |
| 4,206,151 | 6/1980 | Grudzinskas | 568/367 |
| 5,231,222 | 7/1993 | Papa et al. | 560/265 |

FOREIGN PATENT DOCUMENTS 44-017915 6/1969 Japan .
57-081436A2 6/1981 Japan .

OTHER PUBLICATIONS

"Activated Alumina for Removing Dissolved Organic Compounds" by Abraham S. C. Chen et al., Journal of American Waterworks Association, vol. 81 (1), pp. 53–60 (1989).

*Primary Examiner*—Arthur C. Prescott
*Attorney, Agent, or Firm*—Wayne A. Jones; Richard D. Fuerle

[57] ABSTRACT

Disclosed is a method of making a liquid ether acetate. After reacting acetic acid with the corresponding ether alcohol, the resulting mixture of ether acetate, water, acetic acid, and ether alcohol is, with no distillation, contacted with alumina. Particular ether acetates that can be treated include ethylene glycol monobutyl ether acetate and diethylene glycol monobutyl ether acetate. The treated acetates are more stable to hydrolysis after they have been passed over a bed of alumina.

20 Claims, No Drawings

ACETIC ACID REMOVAL FROM LIQUID ETHER ACETATES

BACKGROUND OF THE INVENTION

This invention relates to the removal of acetic acid from liquid ether acetates. In particular, it relates to contacting liquid ether acetates with alumina.

Ethylene glycol monobutyl ether acetate (EBA, also known as butoxyethyl acetate or butyl cellosolve acetate) is a colorless high boiling liquid which is used as a solvent for nitrocellulose lacquers, epoxy resins, multicolored lacquers, as a film coalescing aid for polyvinyl acetate latex, and for other purposes. EBA is made by reacting acetic acid with ethylene glycol monobutyl ether alcohol (EB):

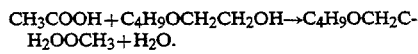

Fractional distillation is used to separate the product from the reactants and from the water that is formed. Upon standing for a period of time hydrolysis, the reverse reaction, occurs, which contaminates the EBA with acetic acid. Commercially prepared EBA typically consists of about 98 to about 99 wt % EBA, about 1 wt % ethylene glycol monobutyl ether alcohol, and about 200 to about 1000 pmm of acetic acid. Many users of EBA require an acetic acid content of less than 200 ppm because the presence of acetic acid in EBA can cause corrosion and adherence problems and can adversely affect the properties of the inks, paints, emulsions, lacquers, etc., in which the EBA is used.

At the present time, acetic acid is removed from EBA by fractional distillation under vacuum, an expensive and time-consuming process. To reduce the acetic acid concentration, a significant amount of EBA is distilled off along with the acetic acid and the overhead EBA-acetic acid mixture must be recycled back to the synthesis step or re-distilled to recover the material. The recycling or re-distillation significantly reduces the process productivity.

Efforts have been made to stabilize EBA and prevent it from undergoing hydrolysis and forming acetic acid (see for example, EPO application No. 521,488.) U.S. Pat. application Ser. No. 08/096,395, filed Jul. 26, 1993, by Steven Qi et al. describes the addition of an amine to stabilize EBA, but the presence of an amine in EBA may be undesirable for some applications. Also, while the amine stabilizes EBA, it does not reduce the acetic acid concentration in the EBA and therefore fractional distillation of the crude EBA product is still necessary.

SUMMARY OF THE INVENTION

We have discovered that acetic acid can be removed from EBA and other liquid ether acetates by contacting them with alumina. For an impurity to be removed by such a process, it generally must be retained by the solid adsorbent while other components in the stream are not adsorbed or do not interfere with the target adsorption. It is, however, very difficult to predict which materials will adsorb acetic acid but will not adsorb EBA or EB, as EB could be more than 1% in EBA. The adsorbent also should not promote any chemical reactions such as saporification. Thus, finding a proper adsorbent very often is an art more than a science. During this discovery many other adsorbent materials, including activated carbon, zeolites, molecular sieves and ion exchange resins, were tried but were found to be unsuitable for processing this stream. Not only is the process of this invention relatively simple and easy to perform, but we have found that the alumina can be easily regenerated and re-used with the same efficiency.

Surprisingly, we have found that since treatment with alumina reduces the acetic acid concentration, a large portion of the fractional distillation of the crude EBA product can be eliminated; the process time and utility can thus be reduced, which is a considerable cost savings. Even more surprising, we have found that once the acetates have been treated with alumina they are stable and no longer undergo significant hydrolysis even in the presence of moisture. As of now, we have no confirmed explanation for this phenomenon.

DESCRIPTION OF THE PREFERRED EMBODIMENT

Acetates that can be treated using the process of this invention are ether acetates that are liquid at room temperature. They can be prepared by reacting acetic acid with the corresponding ether alcohol. Preferred ether acetates have the general formula

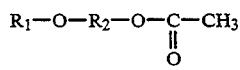

where $R_1$ is alkyl from $C_1$ to $C_{10}$ and $R_2$ is —$C_2H_4$— or —$C_2H_4$—O—$C_2H_4$—. Preferably, $R_1$ is $C_1$ to $C_4$ and $R_2$ is —$C_2H_4$— as those ether acetates are more commercially available. Examples of ether acetates that can be treated using the method of this invention include EBA, ethylene glycol monoethyl ether acetate (EEA), diethylene glycol monobutyl ether acetate (DBA), ethylene glycol monomethyl ether acetate, ethylene glycol diacetate, and ethylene glycol monoacetate. The most preferred acetates are EEA, EBA, and DBA as they are widely used commercially.

Alumina is sold as basic alumina, acidic alumina, and neutral alumina. Either basic alumina or neutral alumina can be used in this invention, although neutral alumina seems to work better. The alumina is preferably activated, which is accomplished by heating to drive off moisture. Alumina comes in various particle sizes and we have found that the finer particle size alumina (greater than 8 mesh size) will remove more acetic acid. The amount of acetic acid that can be removed depends upon the concentration of the acetic acid in the acetate. Alumina can generally remove more acetic acid if the acetic acid concentration in the acetate is higher. While the amount of alumina required will depend on the concentration of acetic acid in the acetate, we have found that 1 gm of alumina will remove about 0.01 gm of acetic acid at a concentration of acetic acid of about 200 ppm when alumina of a large particle size (10 to 14 sieve size) is used.

The acetate can be contacted with the alumina in various ways, including mixing the alumina with the acetate followed by settling and decanting of the acetate, but it is usually most convenient to pass the acetate through a bed of the alumina. The slower the acetate is passed through the bed the more acetic acid will be removed. Preferably, the acetates are treated at room temperature although the process of this invention will also work at higher and lower temperatures. The acetic acid in the effluent can be monitored and when it exceeds a pre-subscribed limit the flow of acetate can be switched to another alumina bed. Alternatively, once a determination has been made of the volume of acetate that a particular alumina bed can treat, a fresh bed can be used after that volume of acetate has been processed.

The used alumina can be regenerated by washing with water or an aqueous solution of sodium hydroxide and drying. Regenerated alumina performs as efficiently as virgin alumina. The acetate product is very stable, even in the presence of moisture and even though no stabilizers, such as amines, are added.

The following examples further illustrate this invention.

EXAMPLE 1

To a commercially produced sample of EBA containing about 1% EB was added 1000 ppm of water. The initial acetic acid level increased from 175 ppm to 590 ppm after eighteen days then to 1473 ppm after than eight months. To a flask was added a 150 gm of this hydrolyzed sample and 37.5 gm of neutral 507-CL Camag alumina powder of 60 to 150 alumina was filtered off. The filtrate was titrated and was found to contain only 10 ppm of acetic acid. The EB content of the filtrate was unchanged. To this filtrate was added 1000 ppm of water. After 31 days the acetic acid level of the filtrate was only 12 ppm. This experiment demonstrates that treatment with alumina produces a very stable EBA, even in the presence of substantial moisture.

EXAMPLE 2

Example 1 was repeated using 6.2 gm of Fischer A50-212 neutral activated alumina having 8 to 14 mesh size with 25 gm of the hydrolyzed EBA. The treated EBA has an acetic acid level of 31 ppm.

EXAMPLE 3

A 1.4 cm diameter column was packed to a height of 5 cm with 5.4 gm of Fischer A50-212 neutral activated alumina of 8 to 14 mesh size. A stream of EBA containing 220 ppm of acetic acid was fed from the top of the column at various flow velocities and the effluent was analyzed for acidity. The following table gives the flow rate and effluent acetic acid level.

| Flow Rate (ml/min) | Acetic acid level in effluent (ppm) |
| --- | --- |
| 3.4 | 84 |
| 7.5 | 149 |
| 13.4 | 176 |

The effluent EB content of the samples was unchanged. The table shows that a lower flow rate results in a larger reduction in acetic acid level. About 700 to 900 gm of EBA was treated and the overall acetic acid level was reduced about 50 ppm. The breakthrough point was at about 1000 gm of EBA effluent. The capacity was about 0.01 gm acetic acid absorbed per gram of alumina.

When the breakthrough point was reached, the EBA in the column was drained and purged with nitrogen. The column was heated to 105° C. and washed with 5×150 ml hot water. The column was again purged with nitrogen and dried at 120° C. for one hour. About 1000 gm of EBA containing 232 ppm acetic acid was fed through the regenerated column at 15 ml/min at room temperature. The average effluent had 190 ppm acetic acid. Both the treated and the untreated EBA were spiked with 1000 ppm water to test their stability.

After 10 days the untreated EBA had an increase of 32 ppm in acidity while the treated EBA had an increase of only 2 ppm in acidity. No deterioration in the performance of the alumina was observed after 3 regenerations.

EXAMPLE 4

In this example, 0.5 g activated basic alumina spherical particles ($\frac{1}{8}$" size, surface modified, Grade CL-750) from Discovery Chem, Inc. was stirred with 105.8 g EBA containing 332 ppm acetic acid. The alumina also contained 0.3 to 2% $Na_2O$ and 0.02 to 0.04% $SiO_2$. After 2 days of stirring, the alumina was removed. The acetic acid content of the EBA was reduced to 229 ppm.

We claim:

1. A method of making a liquid ether acetate comprising reacting acetic acid with the corresponding ether alcohol to form a mixture of the liquid ether acetate, water, unreacted acetic acid, and unreacted ether alcohol and, without distilling said mixture, contacting it with alumina.

2. A method according to claim 1 wherein said liquid ether acetate has the formula $$R_1-O-R_2-O-\underset{\underset{O}{\|}}{C}-CH_3$$

where $R_1$ is alkyl from $C_1$ to $C_{10}$ and $R_2$ is $-C_2H_4-$ or $-C_2H_4-O-C_2-H_4-$.

3. A method according to claim 2 wherein $R_1$ is $C_1$ to $C_4$ and $R_2$ is $-C_2H_4-$.

4. A method according to claim 1 wherein said liquid ether acetate is ethylene glycol monobutyl ether acetate.

5. A method according to claim 1 wherein said liquid ether acetate is diethylene glycol monobutyl ether acetate.

6. A method according to claim 1 wherein said alumina is basic alumina.

7. A method according to claim 1 wherein said alumina is neutral alumina.

8. A method according to claim 1 including the additional last step of regenerating said alumina.

9. A method according to claim 8 wherein said alumina is regenerated by washing it with water and drying it.

10. A method according to claim 8 wherein said alumina is regenerated by washing it with an aqueous solution of sodium hydroxide and drying it.

11. A liquid ether acetate treated according to the method of claim 1.

12. A method of making ethylene glycol monobutyl ether acetate comprising reacting acetic acid with ethylene glycol monobutyl ether alcohol to form a mixture of ethylene glycol monobutyl ether acetate, water, unreacted acetic acid, and unreacted ethylene glycol monobutyl ether alcohol and passing said mixture, without distilling it, through a bed of alumina.

13. A method according to claim 12 wherein said alumina is basic alumina.

14. A method according to claim 12 wherein said alumina is neutral alumina.

15. A method according to claim 12 including the additional last step of regenerating said alumina.

16. A method according to claim 15 wherein said alumina is regenerated by washing it with water and drying it.

17. A method according to claim 15 wherein said alumina is regenerated by washing it with an aqueous solution of sodium hydroxide and drying it.

18. A liquid ether acetate made according to the method of claim 12.

19. A method of removing acetic acid from a liquid ether acetate comprising contacting said liquid ether acetate with alumina.

20. A liquid acetate treated according to the method of claim 19.

* * * * *